(12) United States Patent
Arslan et al.

(10) Patent No.: US 11,077,295 B2
(45) Date of Patent: Aug. 3, 2021

(54) SYSTEM FOR CONNECTING A BLOOD PUMP TO A HEART

(71) Applicant: Berlin Heart GmbH, Berlin (DE)

(72) Inventors: Nedim Arslan, Berlin (DE); Heiko Gundlach, Berlin (DE); Benjamin Daniel Kaebe, Perth (AU); Gerhard Lauterbach, Berlin (DE); Michael Matthes, Altlandsberg (DE); Kim Peter Winterwerber, Berlin (DE)

(73) Assignee: Berlin Heart GmbH, Berlin (DE)

(*) Notice: Subject to any disclaimer, the term of this patent is extended or adjusted under 35 U.S.C. 154(b) by 312 days.

(21) Appl. No.: 15/758,919

(22) PCT Filed: Sep. 12, 2016

(86) PCT No.: PCT/EP2016/071469
§ 371 (c)(1),
(2) Date: Mar. 9, 2018

(87) PCT Pub. No.: WO2017/042392
PCT Pub. Date: Mar. 16, 2017

(65) Prior Publication Data
US 2019/0038819 A1 Feb. 7, 2019

(30) Foreign Application Priority Data

Sep. 11, 2015 (EP) .................................. 15184794

(51) Int. Cl.
*A61M 60/857* (2021.01)
*A61M 60/148* (2021.01)

(52) U.S. Cl.
CPC ........ *A61M 60/857* (2021.01); *A61M 60/148* (2021.01)

(58) Field of Classification Search
CPC . A61M 1/1008; A61M 60/857; A61M 60/148
See application file for complete search history.

(56) References Cited

U.S. PATENT DOCUMENTS 6,319,231 B1 11/2001 Andrulitis
2002/0095210 A1 7/2002 Finnegan et al.
(Continued)

FOREIGN PATENT DOCUMENTS

EP     2 524 709 A1   11/2012
WO    WO 00/47270 A2   8/2000
(Continued)

OTHER PUBLICATIONS

International Search Report with English translation, dated Dec. 14, 2016, pp. 1-7, Issued in International Patent Application No. PCT/EP2016/071469, European Patent Office, Rijswijk, Netherlands.
(Continued)

*Primary Examiner* — George R Evanisko
(74) *Attorney, Agent, or Firm* — Brinks Gilson & Lione

(57) ABSTRACT

A system is provided for connecting a blood pump to a heart, the system comprising: a blood pump for conveying blood, wherein the blood pump comprises a first tubular portion and a second tubular portion, and between the first and the second tubular portion, there is a flange-shaped portion; and comprising a connector having a tubular connector portion extending in an axial direction between a distal end and a proximal end having a lumen for receiving the first tubular portion of the blood pump, and having a flange-shaped connector portion arranged at the distal end for fastening the connector to an organ.

15 Claims, 7 Drawing Sheets

(56) References Cited

U.S. PATENT DOCUMENTS

2014/0067057 A1* 3/2014 Callaway .............. A61M 1/122
623/3.26
2014/0316426 A1 10/2014 Göllner et al.

FOREIGN PATENT DOCUMENTS

| WO | WO 2006/019755 | 2/2006 |
| WO | WO 2014/036060 | 3/2014 |

OTHER PUBLICATIONS

First Office Action and Search Report with English translation, issued in CN Application No. 201680059235.5, dated Mar. 19, 2020, pp. 1-19, China National Intellectual Property Administration, Beijing, CN.

* cited by examiner

SYSTEM FOR CONNECTING A BLOOD PUMP TO A HEART

CROSS-REFERENCE TO RELATED APPLICATIONS

This application is a 371 nationalization of international patent application PCT/EP2016/071469 filed Sep. 12, 2016, which claims priority under 35 USC § 119 to European patent application 15184794.4 filed Sep. 11, 2015. The entire contents of each of the above-identified applications are hereby incorporated by reference.

TECHNICAL FIELD

The present application relates to a system for connecting a blood pump to a heart, comprising a blood pump and a connector, which can be fastened to an organ, for example to a heart, and into which the blood pump can be inserted.

BACKGROUND

Heart assist pumps, such as ventricular assist devices (VADs), have long been known in the prior art. In addition, there have been numerous suggestions for connecting pumps of this kind to an organ, for example to a heart.

A large number of VAD connector systems comprise a connector which for example is anchored to an apex of a left ventricle, for example with the aid of a suture or a spiral spring. An opening is then cut into the ventricle, through which opening the blood pump can be slid into the ventricle.

Many systems are known in the prior art in order to ensure a secure fastening of the blood pump to the connector. For example, U.S. Pat. No. 6,802,806 B2 presents a VAD connector system in which the heart pump or a cannula of a heart pump can be screwed to a connector. Although screwing allows for a secure fastening, it has the disadvantage that screwed connections, for example in the human body, are associated with difficulties.

A further solution is presented for example in U.S. Pat. No. 8,403,823 B2, which suggests connecting an inlet port of a blood pump to a connector by means of pins or screws. Although here as well a secure connection can be ensured, it is difficult to introduce the screws in the body.

A further system is presented in U.S. Pat. No. 8,152,845 B2, which suggests an attachment ring with a cuff fastened thereto, which can be drawn over a tubular portion of a blood pump and which is either securely fastened to the blood pump by means of clamping force or can be fastened to the blood pump by sutures. Although here as well a secure fastening can be ensured, the fastening of the blood pump to the cuff in the body is associated with difficulties.

A further system is presented in U.S. Pat. No. 7,942,805 B2. The system comprises a connector which comprises an inwardly acting locking ring, which can engage radially in a groove of an inlet port. The locking ring is radially constricted here by means of a screw, such that the ring of the connector engages the groove of the inlet port of the blood pump from behind and provides axial fixing. Although a secure fastening is possible with this system, the operation of the screw in the body is associated with difficulties. In addition, there must be a groove on the inlet port of the pump, and this groove must be engaged from behind.

A further system is known from EP 2 5247 09 A1. The system comprises an attachment ring, which inter alia has a ring body with a groove. Two front plates with a spring body arranged between the front plates are arranged on the blood pump. Here, the spring body is formed in such a way that in a first configuration it can be slid onto the ring body and in a second configuration can be clamped, such that the groove of the ring body is engaged from behind. The spring body is configured in such a way that it is held in a guide body and can be spread apart in order to be guided over the ring body, and then the pressure applied to spread apart the spring body is released, such that the spring body engages in the groove of the ring body from behind. A secure engagement of the groove from behind is thus made possible, however the handling is not independent of the radial position of the blood pump.

DETAILED DESCRIPTION

Figure 1:
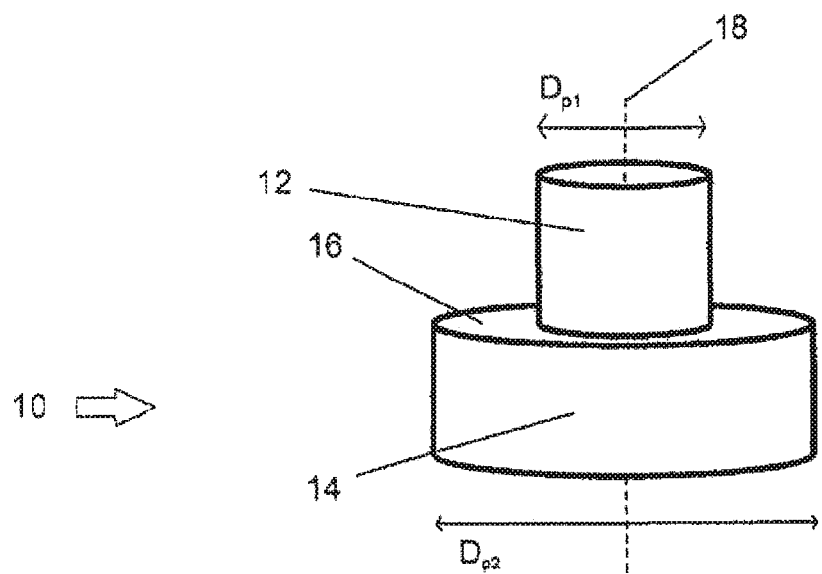
FIG. 1 shows a schematic view of a pump.

A ventricular assist device (VAD) connector system is described herein that offers an alternative to the systems already in existence. The pumps concerned here can be, for example, left VADs (LVADs), right VADs (RVADs) or VADs for both sides (Bi-VADs).

The blood pump for conveying blood comprises a first tubular portion, for example an inlet port, and a second tubular portion, for example an outlet region of a pump, wherein a flange-shaped portion is arranged between the first and second tubular portion. A locking ring expandable in a guiding gap is arranged in the flange-shaped portion of the blood pump, wherein the locking ring is preferably expandable radially. The locking ring is thus guided and configured in the guiding gap such that in a first, unloaded state it has a first diameter and in a second, expanded state has a second diameter, wherein the second diameter is larger than the first diameter.

The system also comprises a connector having a tubular connector portion extending in an axial direction between a distal end and a proximal end, having a lumen for receiving the first tubular portion of the blood pump, and having a flange-shaped connector portion arranged at the distal end for fastening the connector to an organ, such as a heart. A wall surrounding the lumen and comprising an expansion in the form of a latching lug, at least sectionally, is formed in the first tubular connector portion.

The expansion provided in the form of a latching lug widens from the proximal end to the distal end and at its distal end comprises a surface that is to be engaged from behind. If the blood pump is inserted into the lumen with the first tubular portion in the axial direction, the locking ring contacts the proximal end of the expansion provided in the form of a latching lug and is expanded further on account of the profile of the expansion as the blood pump is slid further in the direction of the distal end of the connector, until the latching lug has reached its maximum radial extent, and then snaps onto the surface that is to be engaged from behind and engages it from behind. Since the locking ring is firstly expanded slowly and then "snaps in place", there is a clicking noise, for example, which provides audible feedback to a person inserting the blood pump, indicating that the blood pump is arranged securely on the connector. In addition, vibrations can be induced in the pump housing by the snapping into place of the locking ring, said vibrations providing tactile feedback.

Since the locking ring is expanded by the latching lug without additional pressure being need in order to widen the locking ring, the doctor using the blood pump enjoys simple handling of the pump, since he only has to concern himself with sliding it into position. There is no need for any additional fixing by means of screwing, pressing, or sewing, as was the case in some of the devices according to the prior art. A high level of safety during the operation is hereby ensured, since the person using the pump does not have to grasp the pump at specific points, and instead merely has to insert the pump axially into the lumen.

Since the tubular portions are usually cylindrical portions, it is additionally possible, when sliding the first tubular portion into the lumen, to choose a free radial orientation of the pump adapted to the anatomy of the body. A prior orientation of the connector relative to the blood pump is unnecessary. Since the locking ring engages the latching lug from behind and the first diameter of the locking ring can be selected such that the pump is still freely rotatable, the blood pump can be freely rotated once the expansion of the connector provided in the form of a latching lug has been engaged from behind by the locking ring. Since the locking ring in a second, expanded state does not (anymore) engage the wall or the expansion provided in the form of a latching lug from behind, the pump can also be removed again as required and moved away from the connector in the axial direction.

The locking ring thus engages in the latching lug on the outer side of the connector wall. It is possible in this way that the first tubular portion slid into the lumen of the connector can be formed without a groove. A ring seal can be arranged between the inner wall of the connector and the first tubular portion of the blood pump, which ring seal produces a fluid-tight seal between the blood pump and connector. For this purpose, the inner wall of the connector or the tubular portion of the blood pump can comprise a groove with a ring seal, for example.

In a further aspect of the application, the system for connecting a blood pump to a heart comprises a blood pump for conveying blood, wherein the blood pump comprises a first tubular portion and a second tubular portion (14), and a flange-shaped portion is provided between the first and the second tubular portion. A connector having a tubular connector portion (34) extending in an axial direction between a distal end and a proximal end, having a lumen for receiving the first tubular portion of the blood pump, and having a flange-shaped connector portion arranged at the distal end for fastening the connector to an organ is also provided. The blood pump comprises a first, toothed portion and the connector comprises a second, toothed portion corresponding to the first portion, such that the blood pump is rotationally fixed relative to the connector when the first and the second portion engage in one another.

By means of the toothed portions, the blood pump slid into the connector can be held in a rotationally fixed manner.

Here, the axial height of the teeth in the direction of a common axis of the blood pump and of the connector can be selected in such a way that this height is greater then a potential axial play of the blood pump within the connector in the fastened state of the blood pump. The blood pump is thus prevented from being held rotatably within the connector. Alternatively or optionally, the axial height of the teeth can be selected in such a way that the axial height is smaller than a length of the portion of the blood pump held in the connector. The axial height of the teeth is preferably such that the blood pump is rotatable again when removed over only a small axial distance, for example of less than 15 mm, preferably less than 10 mm, less than 5 mm, or less than 3 mm. In the event of a possible orientation in the sense of a rotary orientation about the coaxial axis of the connector and of the blood pump in the connector, the blood pump thus still remains connected to the connector in a blood-tight manner, such that no blood can pass directly between the connector and the blood pump from the heart.

The toothed region can be arranged merely along an angular portion of less than 360°. A plurality of portions can also be arranged around the connector. In a simple embodiment, however, the toothed region is applied over an angular region of 360° in the form of a closed circle or ellipsis. The toothed region can have one or more toothed profiles and at least two teeth the regions corresponding to one another.

For example, a toothed profile can be understood to mean a sawtooth profile, a wave profile, or the like. The axial height of a tooth or tooth profile can be measured for example axially from the axial tooth tip or wave crest to the tooth base or wave trough.

In this embodiment, a locking ring either on the blood pump (or in the connector) can radially engage in a groove for example or radially press against the surface of the connector (or the blood pump), such that a secure connection or axial mounting between the blood pump and the connector is provided. Examples of a connection of this kind are the examples in this application or those known from the prior art cited in this application. The prevention against rotating is ensured by the toothed regions.

Further exemplary embodiments are explained hereinafter below.

In one embodiment, the expansion of the wall provided in the form of a latching lug is formed such that it surrounds the wall fully. In this embodiment the expansion provided in the form of a latching lug is preferably a closed latching lug extending in the axial direction from the proximal end to the distal end. In this exemplary embodiment it is also advantageous when the wall of the lumen is likewise uninterrupted peripherally. In other exemplary embodiments, it is possible however that the expansion is arranged on fingers extending in the axial direction, said fingers being distanced from one another. In this embodiment, less material is indeed used, however the stability of the fingers is not as great as a wall that is uninterrupted peripherally.

In a further embodiment, the latching lug is configured such that it comprises a flat portion at a proximal end, which flat portion corresponds with a flat region of the flange-shaped portion of the blood pump, such that these flat regions lie flat against one another. A stop lying in the axial direction is hereby formed, such that the pump is prevented from being slid too far into the connector. At the same time, the flat portions can be selected such that, on account of said regions lying flat against one another, the position of the pump on the connector is stabilised and excess wobbling of the pump is prevented.

In a further embodiment the guiding gap is configured such that it has a width corresponding to a height of the locking ring, preferably an axial height of the locking ring, such that the locking ring is fixed on the blood pump in the axial direction. In this way, it can be ensured that the locking ring performs merely a radial movement, but not a significant axial movement. The gap width of the guiding gap is selected here, however, such that the locking ring can be radially moved in the guiding gap with little friction.

In a further exemplary embodiment, the expansion and the locking ring are selected such that the blood pump, in the first state engaging the latching lug from behind, is held rotatably about the axial direction. In this way, the blood pump can be rotated into the desired position after having been securely connected to the connector.

Alternatively to the rotatable mounting, the blood pump and connector can be configured in such a way that they are arranged non-rotatably relative to one another in the first state, i.e. in the state guided one inside the other. In one embodiment, the blood pump comprises a first toothed portion. The connector has a second toothed portion, wherein the two toothed portions correspond with one another, i.e. the teeth of the respective portions can engage in one another. When the teeth engage in one another, the connector and the blood pump are no longer rotatable relative to one another, i.e. they are rotationally fixed relative to one another. In order to rotate the blood pump relative to the connector, the locking ring must be released, and the blood pump must be removed from the connector in the axial direction. As soon as the toothed portion of the blood pump no longer engages in the toothed portion of the connector, the blood pump can be rotated again relative to the connector. As soon as the desired orientation of the blood pump has been set, the blood pump is pushed back into the connector, and the tooth portions engage in one another.

In a development of the toothed portions of the blood pump and/or of the connector, these are arranged rotationally symmetrically as considered in the axial direction. It is hereby ensured that a non-rotatable fixing is possible in any arbitrary orientation of the blood pump relative to the connector. In a development, both tooth portions are formed here rotationally symmetrically and correspondingly to one another.

In a further exemplary embodiment, the guiding gap is open in a radial direction. In this way, the locking ring, when assembling the blood pump, can be slid into the guiding gap at a relatively late moment in time. However, this sliding-in of the locking ring can be performed outside the body or already at the time of manufacture of the pump. In addition, when expanding the locking ring, an open guiding gap means that tissue which has collected between the locking ring and the pump can be displaced from the open guiding gap and the locking ring can thus still be expanded radially, even after having remained in the body for a relatively long period of time. This is necessary for example when changing a pump or in the case of explantation.

In a further exemplary embodiment, the flange-shaped portion of the blood pump has a radial stop, which prevents the locking ring from being constricted to a diameter smaller than the first diameter. This is helpful in particular prior to implantation, since damage to the locking ring prior to implantation can be prevented. The stop can be given either by the flange-shaped portion itself, or can be provided with the aid of a further component, i.e. a stop ring.

In a further exemplary embodiment, the locking ring has an angled profile, for example an L-shaped profile, wherein a first portion of the locking ring is configured to engage the expansion provided in the form of a latching lug from behind, and a further portion, which is angled for engagement from behind, is designed such that it lies radially against the stop of the blood pump and is supported. As a result of the support, a narrowing of the locking ring to a diameter below the first diameter can be prevented.

In a further exemplary embodiment the locking ring is an open locking ring and comprises an angular segment of for example more than 270°, preferably more than 300°, preferably more than 330°, in some exemplary embodiments an open overlapping locking ring with an angular segment of more than 390°. At one end, the locking ring is fixed to the flange-shaped portion of the blood pump, preferably fixed in an integrally bonded or interlocking manner. The locking ring for example can thus be welded to the blood pump, held rotatably in a pin, or fixed in a similar or equivalent way.

In a further embodiment, the locking ring comprises a grip element for transferring the locking ring from the first state into the second state. With the aid of a grip element protruding radially from the flange-shaped portion of the blood pump, said locking ring can be expanded from the first state into the second state.

In a further embodiment, a further grip element is arranged on the blood pump in a manner corresponding to the first grip element, such that, when the grip element of the locking ring and the grip element mounted on the pump are gripped and the two elements are then guided towards one another, the locking ring is expanded. The explantation of the blood pump is hereby simplified considerably. However, it should be noted that the grip elements are necessary merely for explantation or for removal of the pump. When the pump is slid into the connector element, the locking ring is expanded by the latching lug. The grip element or the grip element of the blood pump corresponding thereto, is merely necessary in order to expand the locking ring from the surface of the latching lug engaging from behind.

As already mentioned, the guiding gap can be open in a radial direction. Alternatively or additionally, the blood pump, in the flange-shaped portion or in the second tubular portion, can have further openings for displacement of tissue disposed between the locking ring and the blood pump. The explantation of the pump is hereby simplified. In some embodiments just one opening can be provided, and in other embodiments more than one opening can be provided.

in a further embodiment, the system comprises a casing that can be drawn over the blood pump. The expression "can be drawn" is to be understood here to mean that the casing for example is flexible and is only pulled onto the pump later. The casing comprises at least one tongue, preferably protruding inwardly, which engages in the at least one opening of the flange-shaped portion of the blood pump. For example, the casing can be made of silicone or another soft, biocompatible material. Since the tongue protrudes into the at least one opening, the opening can be prevented from becoming blocked with ingrowing tissue. In the case of explantation of the blood pump, the casing can be removed and the little, remaining tissue can be easily displaced from the openings. It should be noted that the applicant shall pursue the casing within the scope of a divisional application independently for use with a VAD system. The same is true for the toothed portions of the connector and the blood pump.

In a further embodiment, the first tubular portion of the blood pump comprises a groove, in which a sealing element, for example in the form of a ring seal, is arranged. Alternatively, the connector can comprise a groove or a ring seal on the inner side of the wall surrounding the lumen.

Some exemplary embodiments of a VAD connector system will be explained hereinafter. It should be noted at this juncture that both the blood pump per se and the connector per se form independent parts of the application and can be pursued within the scope of further applications.

FIG. 1 schematically shows a blood pump 10, which comprises a first tubular portion 12 and a second tubular portion 14, which are coupled to one another by means of a flange-shaped portion 16. The three portions 12, 14 and 16 are oriented coaxially along the axis 18. The first tubular portion 12 can be used here for example as an inlet port and, depending on the used connector system, can be inserted for example into a ventricle through the heart wall. The second tubular portion 14 for example comprises a spiral chamber inside and additionally an outlet (not shown here in greater detail), via which the fluid drawn in through the inlet is expelled. In the present exemplary embodiment the tubular portion 12 has an outer diameter $D_{p1}$, which is smaller than the outer diameter of the second tubular portion $D_{p2}$.

Figure 2:
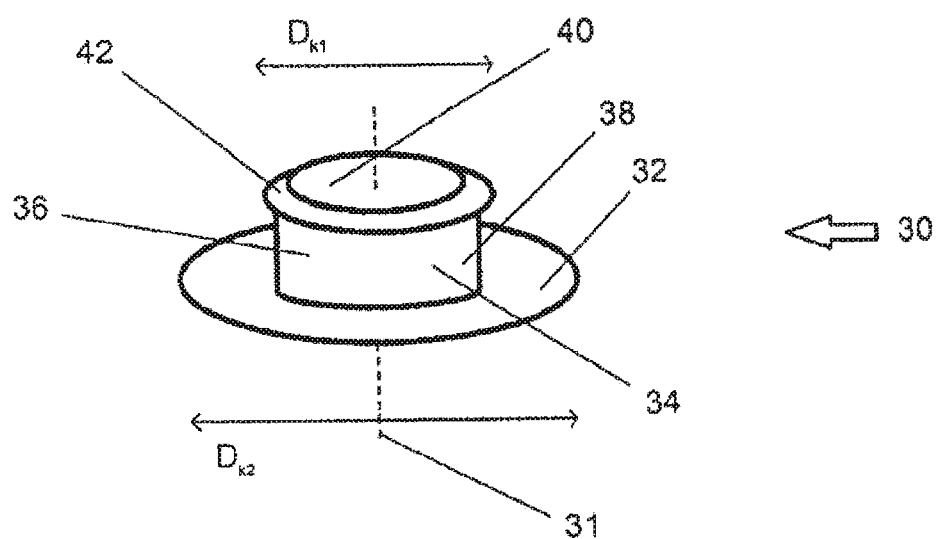
FIG. 2 shows a schematic view of a connector.

In FIG. 2 a connector 30 according to the application is shown schematically. The connector 30 comprises a flange-shaped connector portion 32 and a tubular connector portion 34, which extends along the axis 31 from a distal end, arranged on the flange-shaped portion 32, to a proximal end. The tubular connector portion comprises a wall 36 with an inner face 40, into which for example the first tubular portion 12 of the blood pump 10 of FIG. 1 can be inserted. Furthermore, the wall has an outer face 38, wherein an expansion 42 having a latching lug profile is arranged at the proximal end of the outer face 38. The latching lug profile is formed here such that the radial width or the diameter widens from a proximal end to a distal end, until a surface of the latching lug profile engaging from behind (not shown in greater detail) finishes.

The inner face 38 of the connector 30 has a diameter $D_{k1}$ corresponding to the inlet diameter $D_{p1}$. The flange-shaped connector portion 32 has an outer diameter $D_{k2}$ and can be formed such that it can have on its outer edge, for example, holes for attaching the connector to an organ by means of sutures. The connector 30 for example can be formed uniformly from a single metal or a metal composition or a plastic. Furthermore, the flange-shaped portion 32 in the region of the tubular connector portion can for example consist of a metal, whereas the outer edge of the flange-shaped portion 32 consists of a flexible material that can be easily attached to an organ by means of sutures. The diameter $D_{k2}$ can be selected here in such a way that it is larger than the diameter $D_{p2}$ of the second tubular portion 14 of the blood pump 10 of FIG. 1. An improved stability of the blood pump in the state connected to the connector can thus be achieved.

An illustration of the blood pump 10 in a plane perpendicular to the axis 18 is shown in FIG. 3. The first tubular portion 12, the second tubular portion 14, and the flange-shaped portion 16 arranged therebetween are visible by solid lines. An open locking ring 50 is shown by dashed lines, the grip element 52 of said ring extending radially until outside the second tubular portion 14. The grip element 52 is arranged on a grip end 54 of the locking ring. The locking ring extends over an angular segment of more than 330° from its grip end 54 to the open end 56, where it lies against a stop 58 formed as part of the pump. The stop 58 prevents the locking ring 50 from being able to be further rotated to an unlimited extent in the direction 60 in the event that a force is applied to the grip element in the direction 59. In addition, the L-shaped stop 58 prevents the locking ring from escaping in the radial direction 62. Here, the locking ring 50 can lie loosely in a guiding gap, without being connected to the pump by means of an integrally bonded, frictionally engaged or interlocking connection.

A recess 70, which is likewise annular and the width of which as considered in the radial direction 62 corresponds substantially to the width of the expansion 42 having a latching lug profile, is situated between the tubular portion 12 and the tubular portion 14, in the region of the flange-shaped portion 16. It can be seen that the locking ring, shown in its first, unloaded state, engages in the recess 70 radially. The cooperation between the expansion 42 provided in the form of a latching lug and the locking ring 50 is explained in greater detail with reference to FIG. 5. Optional stop elements 72 are additionally shown in FIG. 3A, said stop elements being arranged on the blood pump, radially outside the locking ring. The stop elements prevent the locking ring from being able to be widened too far radially, and for example can be made of silicone, steel or foam material. These stop elements are also used to provide an additional, outer centring and can also be used in the other exemplary embodiments of the blood pump or system. Furthermore, the locking ring, in the vicinity (for example of a 60° segment, considered in an anticlockwise direction) of the stop 58 has a reduced radial width B1 compared to a width B2 of the locking ring in other segments. As a result, the locking ring releases the expansion provided in the form of a latching lug, even in the region of the stop. The transition of the width of the locking ring from the width B1 to the width B2 can be gradual, as shown, i.e. over a certain angular segment (for example 10°), or can be sudden. The transition can have a linearly or non-linearly increasing width from the width B1 to the width B2.

Figure 3A:
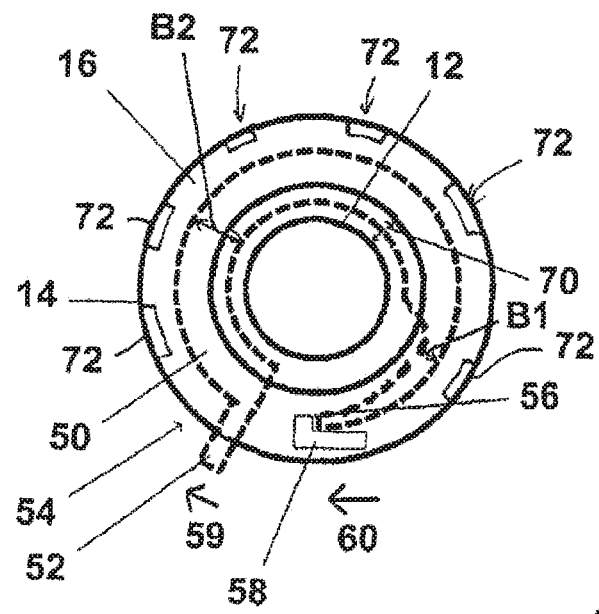
FIGS. 3A-C show a cross-section of a pump with locking ring.
Figure 3D:
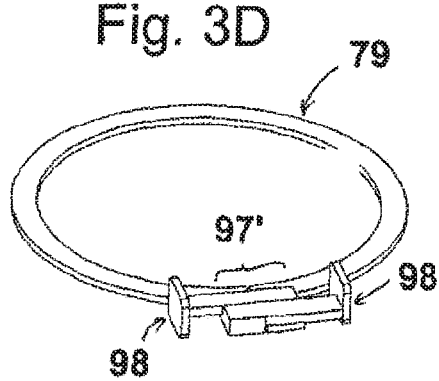
FIG. 3D shows a further exemplary embodiment of a locking ring.
Figure 3B:
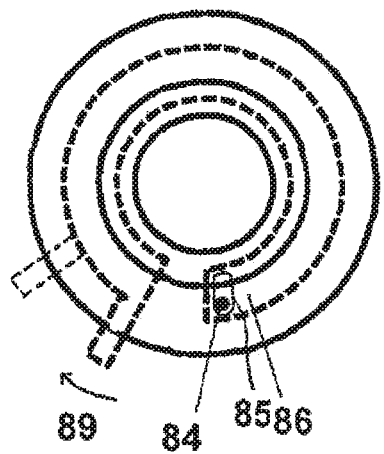

An alternative locking ring 80 is shown in FIG. 3B. This locking ring is substantially identical to the locking ring 50 of FIG. 3A, however it is held in the guiding gap in an interlocking manner by means of a pin 84 connected to the pump and a recess in the locking ring 86 corresponding to said pin. When a force is applied in the direction 89, the locking ring is expanded on the one hand, and the locking ring rotates about the pin 84. Here, the locking ring, in an advantageous embodiment, can have a smaller width within an angular segment, arranged in an anticlockwise direction from the pin 84, of 30° to 100° for example, preferably from 50° to 80°, such that the locking ring does not protrude into the recess 70 in the region of the angular segment. This thus prevents merely a strong expansion of the locking ring from releasing the latching lug of the connector. In order for the locking ring 86 to be sufficiently expanded also at the pin 84, the ring is guided at the pin 84 in a slotted guide 85, which extends along the radial direction of the locking ring. If a force is exerted onto the locking ring in the direction 89, for expansion, the slotted guide end of the locking ring moves over the slotted guide 85 away from the state shown in FIG. 3B until it comes to rest against the pin 84 with the opposite end of the slotted guide.

Figure 3C:
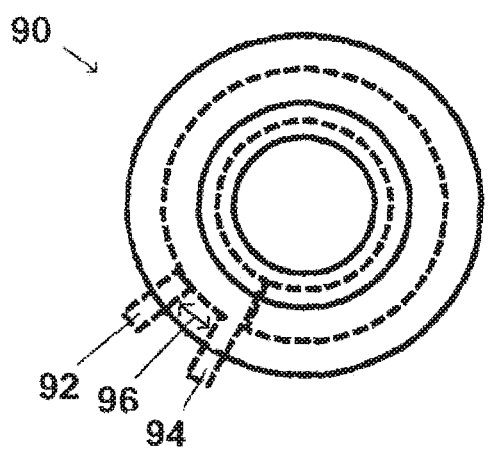

Although an open locking ring is shown in FIGS. 3A and 3B, i.e. said ring comprises an angular segment of less than 360°, as shown for example in FIG. 3C, the locking ring can also enclose an angular region of more than 360°. The locking ring 90 is shown in FIG. 3C here has a first grip element 92 and a second grip element 94. The region 96 lying between the two grip elements is formed here by a part of the locking ring arranged to the left of the grip element 94 and a partial segment of the locking ring connected on the right to the grip element 92, such that the locking ring is present in the region 96 in two layers. By applying pressure to the grip elements 92 and 94 such that they are pushed towards one another, the locking ring can be widened.

A further exemplary embodiment of a locking ring is shown in FIG. 3D. The locking ring 97 is formed similarly to the exemplary embodiment of FIG. 3C. The locking ring 97 has an overlap region 97' and two grip elements 98. The locking ring is expanded by pressing the grip elements 98 towards one another.

Figure 4A:
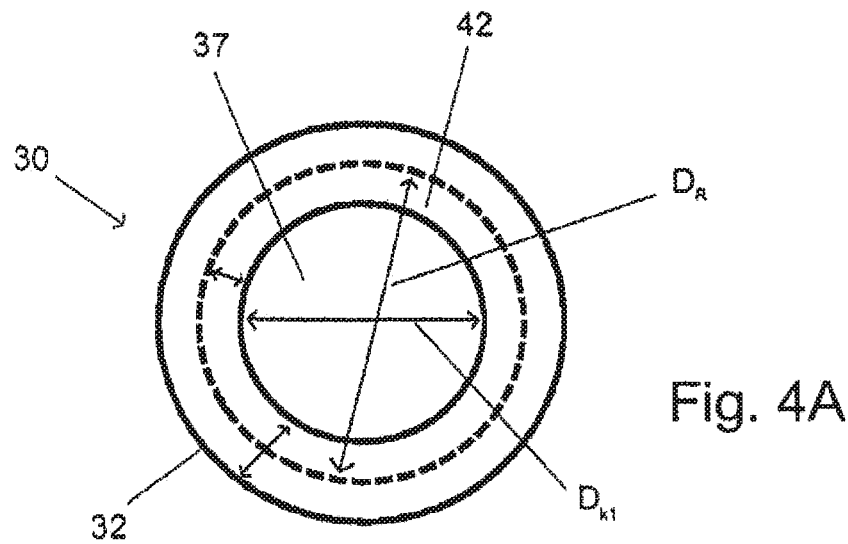
FIGS. 4A-B show a cross-section of a schematic connector.

The connector 30 comprises the flange-shaped portion 32 and, as mentioned in the description of FIG. 2, a tubular connector portion 34. A lumen 37 delimited by the wall 36 of the tubular portion 34 can be seen in FIG. 4A. The lumen 37 has a diameter $D_{k1}$. At the proximal end of the tubular connector portion 34, the expansion 42 provided in the form of a latching lug can be found. The radial diameter of said expansion widens from the diameter $D_{k1}$ to a larger diameter $D_r$.

Figure 4B:
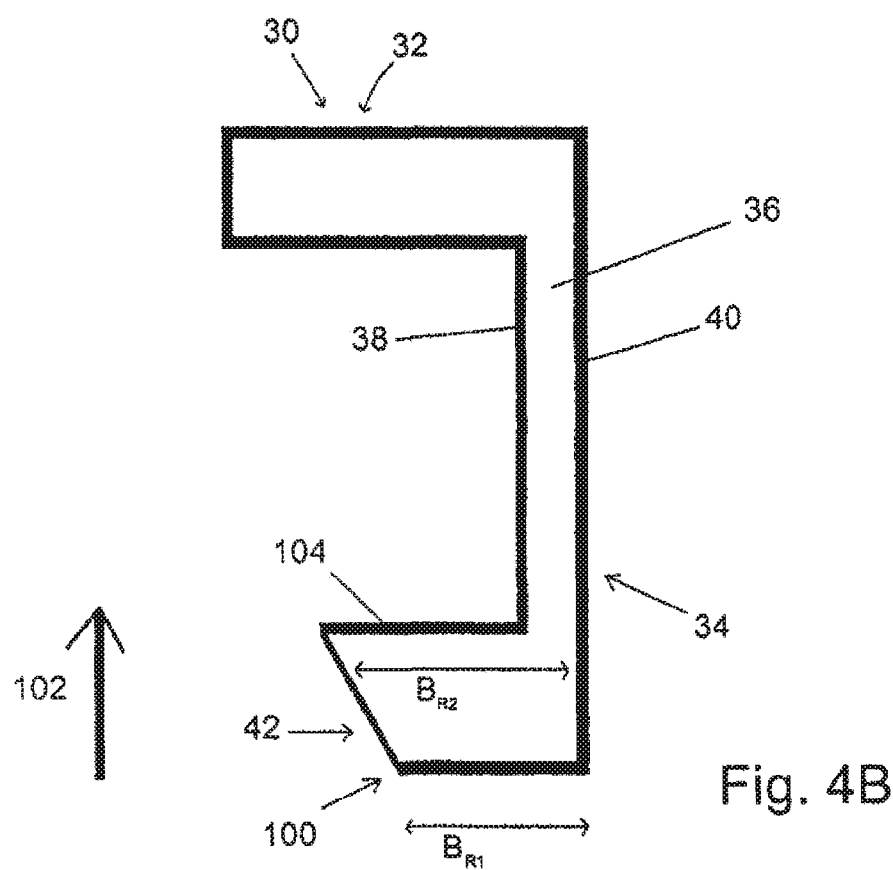

The latching lug profile of the expansion is shown in greater detail in FIG. 4B. The connector 30 has the flange-shaped connector portion 32 and the tubular connector portion 34, which has a wall 36 with an outer face 38 and an inner face 40. The inner face 40 of the tubular portion 34, in the present example, does not have any profiling. The expansion is arranged fully in the region of the outer face of the wall 36. The expansion 42 comprises a latching lug 100, the thickness of which increases in the direction 102, as far as the surface 104 engaging from behind, from a first width $B_{r1}$ to a second width $B_{r2}$.

Alternative profiles of the latching lug profile are also possible. For example, the width $B_{r1}$ can be selected to be substantially equal to zero, such that the latching lug profile has a point at its proximal end.

Figure 5A:
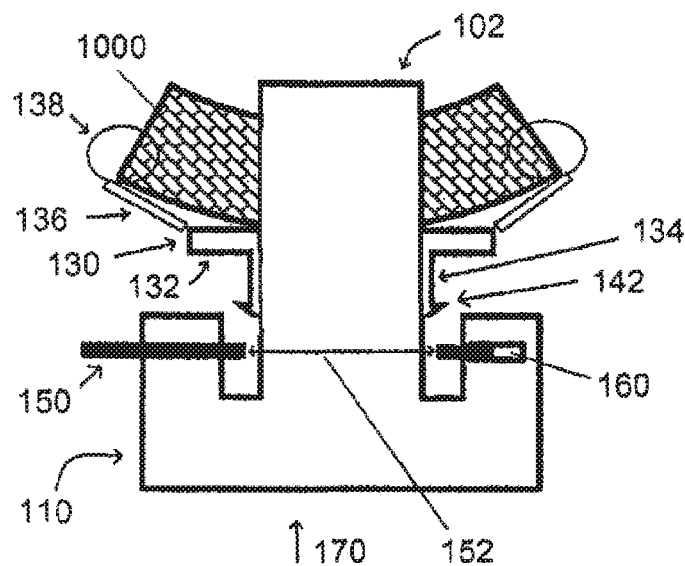
FIGS. 5A-C show various longitudinal sections through a pump-connector system.
Figure 5B:
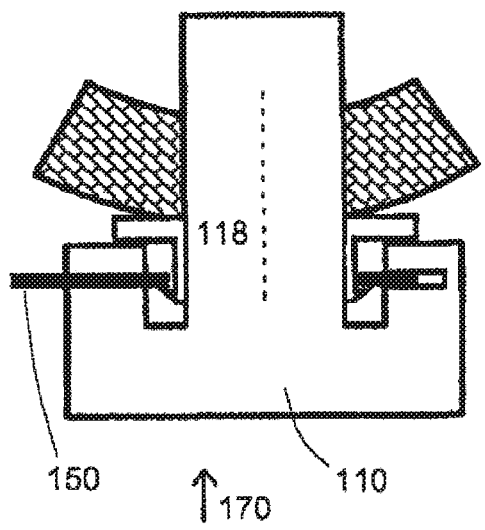
Figure 5C:
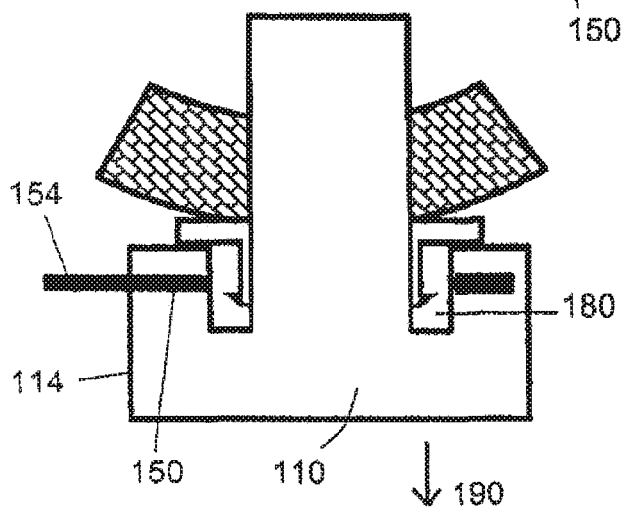

The cooperation of the blood pump with the locking ring and the connector will be illustrated in greater detail on the basis of FIGS. 5A-C.

FIG. 5A shows, inter alia, a heart wall 1000, in which an opening 102 has been formed, for example by punching. A blood pump 110 is inserted into the opening 102 with the aid of a connector 130. Here, the pump 110 corresponds substantially to a pump as has already been explained in detail in FIGS. 1 and 3. The connector 130 corresponds substantially to a connector 30 as shown in FIG. 2. The connector 130 thus likewise comprises a flange-shaped portion 132 and a tubular connector portion 134 with an expansion 142. A flexible ring, which is connected in an integrally bonded manner to the flange-shaped portion 132, is additionally disposed on the radial edge of the flange-shaped portion 132. The ring 136 is sewn to the heart wall 100 with the aid of sutures 138. The blood pump 110 comprises inter alia a locking ring 150, which is guided in a guiding gap 160. In the state shown in FIG. 5A, the blood pump 110 is inserted in the axial direction 170 into the tubular connector portion. It can be seen that the inner diameter 152 of the locking ring in the unloaded state is smaller than the largest outer diameter of the expansion 142. If the blood pump 110 is now slid onto the connector 130 in the direction 170, the locking ring also contacts the expansion and is gradually expanded by the expansion becoming larger in diameter, until the distal end of the latching lug is reached and the locking ring, as shown in FIG. 5B, engages the latching lug from behind. In this state engaging the latching lug from behind, the locking ring is preferably unloaded, i.e. it assumes its form that is given without applied stress.

It is clearly visible to a person skilled in the art that the blood pump 110 is mounted rotatably about the axis 118 in the first, preferably unloaded state of the locking ring shown in FIG. 5B. In order to explant the blood pump 110 for example, a force can be applied by the grip element 154 of the locking ring 150 protruding radially from the second tubular portion 114, such that the locking ring 150 is expanded so that the portion of the tubular connector portion 134 located in the recess 180 is released or the expansion is no longer engaged from behind and the pump 110 can be explanted in the axial direction 190. This is illustrated in FIG. 5C.

Figure 6A:
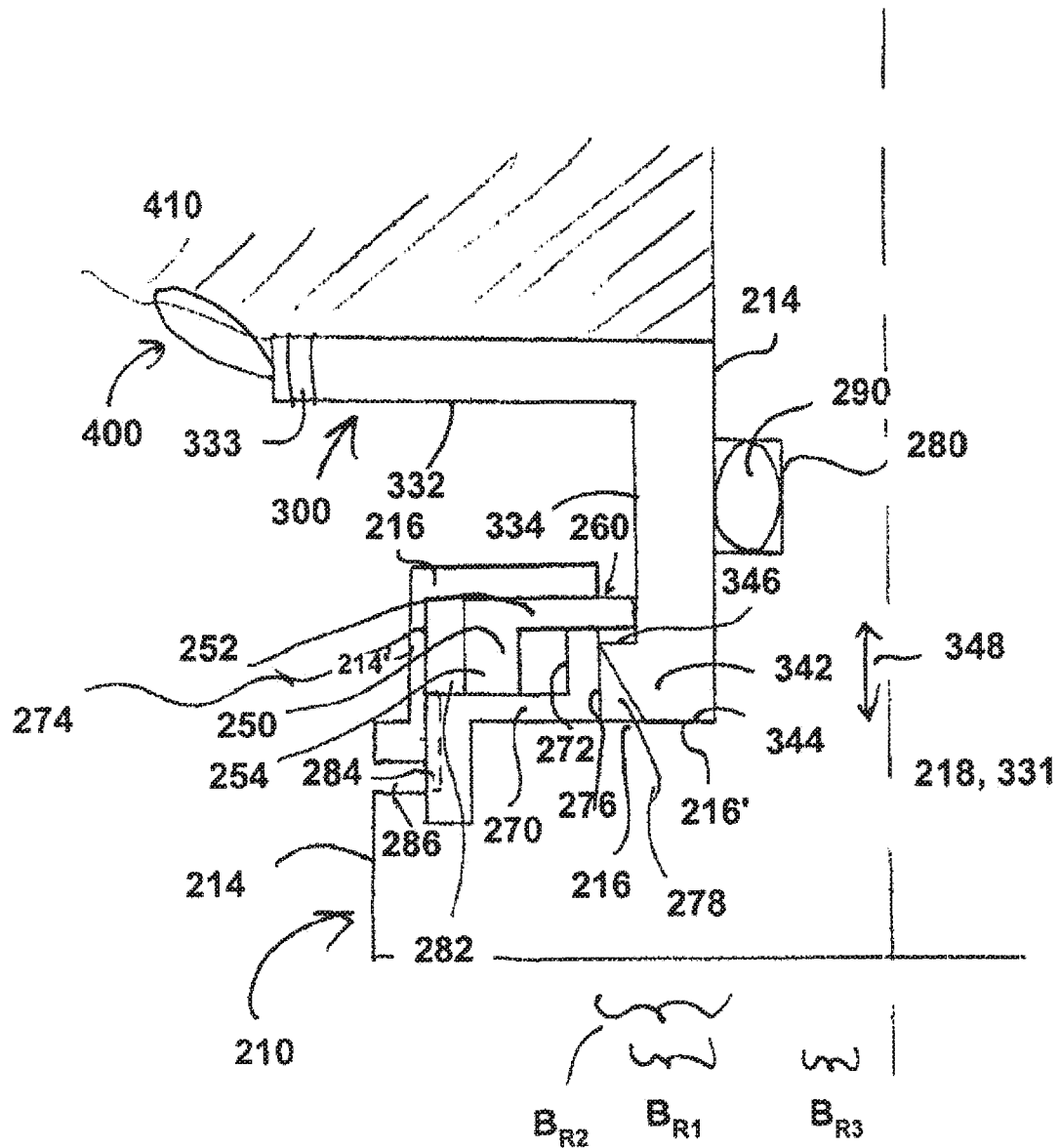
FIGS. 6A-B show a further embodiment of a pump-connector system.

A further exemplary embodiment of a VAD connector system is shown in FIG. 6A. Here, merely a profile detail of the axes 218 of the blood pump and 331 of the connector is shown radially outwardly. The system comprises a blood pump 210 and a connector 300. Here, the connector 300 corresponds substantially to the connectors 30 or 130 already discussed. The connector comprises a flange-shaped portion 332, which comprises openings 333, through which a suture 400 can be guided in order to connect the flange-shaped connector portion 332 to a heart wall 410. The tubular portion 334 of the connector 300 has, at its proximal end, an expansion 342 in the form of a latching lug, which at its most proximal end comprises a flat portion 344, which has a width $B_{r1}$ and which, going in a distal direction, expands over a height 348 to a width $B_{r2}$. At the distal end of the latching lug there is a surface that is to be engaged from behind and that has a width of $B_{r3}$, corresponding to the difference $B_{r2}-B_{r1}$. There is no profiling on the inner wall of the tubular portion 334.

The blood pump 210 comprises a first tubular portion 212, which comprises a groove 280, in which a ring seal 290 is arranged in order to form a seal between the inner wall of the tubular connector portion 334 and the first tubular portion 214. Inter alia, a locking ring 250, which is guided in a guiding gap 260 and which is configured such that it engages the surface 346 that is to be engaged from behind in the unloaded state and can be expanded by means of a mechanism as explained for example in the description of FIG. 5, such that the blood pump 210 can be removed from the connector 300, extends radially from the flange-shaped portion 216 to the second tubular portion 214 of the blood pump 210. The guiding gap 260 receives a first portion 252 of the locking ring 250, wherein the width of the guiding gap in the axial direction of the guiding gap 260 is selected such that the width corresponds substantially to the height of the portion 252 in the axial direction, such that the locking ring 250 has no axial play.

Furthermore, the locking ring 250 comprises an angled region 254, which can be held radially on a stop face 272 of a stop ring 270. Radially opposite and externally of the stop 272 there is an outer radial stop 274 of the flange-shaped portion 116 of the blood pump. A recess 278 is provided between a radially inner region of the stop ring 276 and the first tubular portion 214, which recess has a width $B_{r2}$ corresponding substantially to the width of the largest diameter of the expansion 342. At the proximal end, the expansion 342 has a flat portion 344 corresponding to a flat portion 216' of the flange-shaped portion 216. A cavity 282 is provided between the locking ring 250 and a wall 214' of the blood pump, which cavity can fill with tissue in the event that the blood pump remains in the organic tissue over a longer period of time. So that this tissue does not restrict the movability of the locking ring in the event of explanation, it is provided to introduce channels 284 in the stop ring 270, which channels open out into openings 286 in the second tubular portion 214.

Figure 6B:
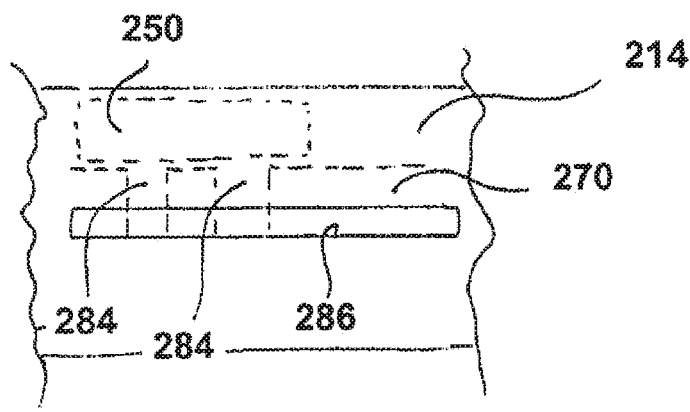

This is shown again in a view in FIG. 6B. The tubular portion 214 has an opening 286, wherein the stop ring 270 has channels 284, through which material situated in the chamber 282 can be expelled in the radial direction as the locking ring expands. In this way, the locking ring is prevented from becoming blocked in an ingrown state.

Figure 7A:
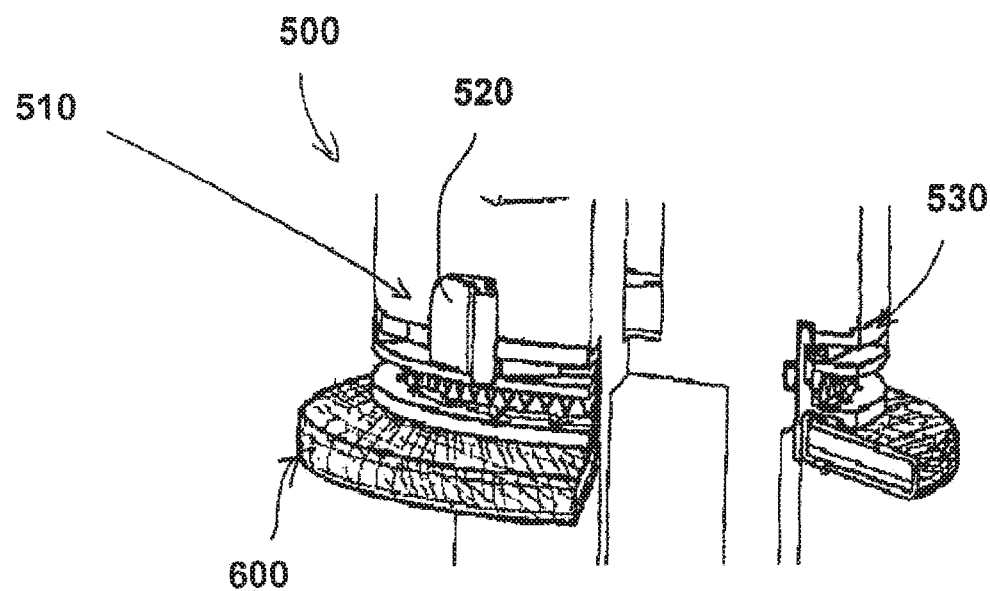
FIGS. 7A-C show a further embodiment of a pump-connector system.
Figure 7B:
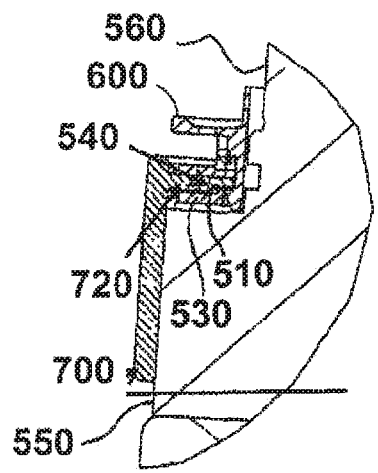
Figure 7C:
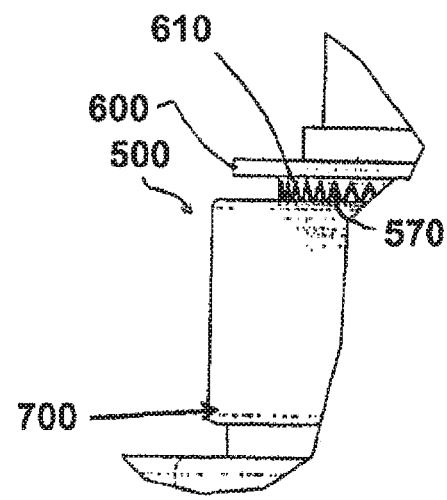

A further alternative of a VAD connector system is shown in FIGS. 7A-7C.

The blood pump 500 is connected to a connector 600. The blood pump here comprises a locking ring 510, which has a grip face 520. Here, the stop ring 530 has been inserted into a guiding gap and defines a guiding gap corresponding substantially to the height of the locking ring. Here, the stop ring was subsequently welded to the pump.

A detail of the pump shown in FIG. 7A is shown in FIG. 7B. Besides the blood pump 500 and the connector 600, a silicone casing 700 that can be drawn over the blood pump is also shown, the function of which will also be described.

The blood pump 500 comprises a flange-shaped portion 540, which has a radius comparable to the second tubular portion 550 and inter alia comprises the aforementioned locking ring and stop ring. Alternatively, the radius of the flange-shaped portion 540 can be selected to be smaller than the radius of the second tubular portion. The flange-shaped portion 540 is merely selected to be larger than the first tubular portion 560. The silicone casing 700 is shown in detail in FIG. 8.

A toothed portion 570 arranged in the blood pump and a toothed portion 610 are arranged on the connector and corresponding to the portion 570 additionally shown in FIG. 7C. In the shown first state (i.e. the blood pump is inserted into the connector), the teeth of the portion 570 are engaged with the teeth of the portion 610 and prevent the blood pump from being able to be rotated relative to the connector, i.e. the blood pump and connector are connected to one another in a rotationally fixed manner. If the blood pump is removed from the connector by the height of the teeth compared to the illustrated state, the blood pump can be rotated again, and another orientation of the blood pump relative to the connector can be set.

In the present example, both the toothed portion 570 and the toothed portion 610 are circular. Any arbitrary orientation of the blood pump relative to the connector can be set as a result, and the orientation can be retained in a rotationally fixed manner.

The toothed portions can be formed for example from a biocompatible material comprising a metal or plastic. The teeth are preferably inflexible or have a sufficient hardness, such that a rotation of the portions relative to one another is not possible.

Figure 8:
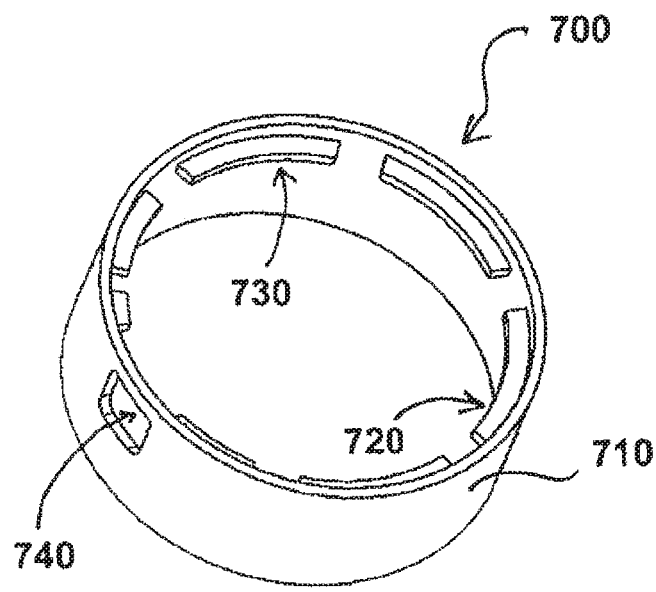
FIG. 8 shows an embodiment of a silicone casing for the system.

The silicone casing 700 is shown in FIG. 8. This comprises a first lateral surface 710, which comes to lie on the second tubular portion 550. Furthermore, the silicone casing comprises a plurality of tongues 720 and 730, which engage in openings of the flange-shaped portion 540 (see FIG. 7B). Due to the engagement of the tongues, tissue cannot fully penetrate the openings and fill the openings, and instead can become ingrown into the gaps between the tongues and the edges of the openings only to a very limited extent, such that the locking ring enables a detachment of the blood pump from the connector in the event of an explantation of the pump, in spite of any ingrown tissue.

Irrespective of the tongues, the silicone casing 700 can comprise an opening 740, through which a grip of the locking ring can protrude.

The present invention relates inter alia to the following aspects:

1. A system for connecting a blood pump to a heart, comprising:
   a blood pump for conveying blood, wherein the blood pump comprises a first tubular portion and a second tubular portion, and between the first and the second tubular portion there is provided a flange-shaped portion;
   a connector having a tubular connector portion extending in an axial direction between a distal end and a proximal end and having a lumen for receiving the first tubular portion of the blood pump, and having a flange-shaped connector portion arranged at the distal end for fastening the connector to an organ, wherein a wall of the first tubular connector portion surrounding the lumen comprises an expansion having a latching lug surrounding the wall, at least sectionally;
   wherein, in the flange-shaped portion of the blood pump, an expandable locking ring is arranged in a guiding gap and is guided and configured in the guiding gap such that in a first state, the locking ring engages the expansion of the wall from behind and, in a second, expanded state, does not engage the wall from behind.
2. The system according to aspect 1, wherein the expansion surrounds the wall fully.
3. The system according to either one of the preceding aspects, wherein the latching lug preferably comprises a flat portion at a proximal end, which flat portion corresponds with the flange-shaped portion of the blood pump.
4. The system according to any one of the preceding aspects, wherein the guiding gap has a width corresponding to a height of the locking ring, such that the blood pump is fixed in the axial direction in the first state.
5. The system according to any one of the preceding aspects, wherein the blood pump in the first state is held rotatably about the axial direction.
6. The system according to any one of aspects 1 to 4, wherein the blood pump comprises a first toothed portion and the connector comprises a second toothed portion corresponding to the first, such that the blood pump is held in the connector in a rotationally fixed manner in the first state.
7. The system according to any one of the preceding aspects, wherein the guiding gap is open in a radial direction.
8. The system according to any one of the preceding aspects, wherein a portion of the flange-shaped portion of the blood pump comprises a stop ring, which preferably centres the locking ring in the second state.
9. The system according to any one of the preceding aspects, wherein the locking ring comprises a portion engaging the expansion from behind and a further portion angled relative to the portion engaging from behind, which angled portion is formed in such a way that the angled portion in the first state is radially supported on a partial segment of the flange-shaped portion or of the first tubular portion.
10. The system according to any one of the preceding aspects, wherein the locking ring is fixed to one end of the blood pump.
11. The system according to any one of the preceding aspects, wherein the locking ring is an open circlip.
12. The system according to any one of the preceding aspects, wherein the locking ring comprises a grip element for transferring the system from the first state into the second state, wherein the blood pump preferably comprises an element corresponding to the grip element, such that a force applied to the grip element in the direction of the corresponding element expands the locking ring.
13. The system according to any one of the preceding aspects, wherein the flange-shaped portion of the blood pump comprises openings to the second tubular portion.
14. The system according to aspect 13, wherein a casing that can be drawn over the blood pump is provided and comprises at least one tongue, which protrudes into the at least one opening.
15. The system according to any one of the preceding aspects, wherein the first tubular portion comprises a groove, in which a sealing element is arranged in such a way that the sealing element lies sealingly against an inner face of the wall.
16. A system for connecting a blood pump to a heart, comprising:
  a blood pump for conveying blood, wherein the blood pump comprises a first tubular portion and a second tubular portion, and between the first and the second tubular portion there is provided a flange-shaped portion;
  a connector having a tubular connector portion extending in an axial direction between a distal end and a proximal end and having a lumen for receiving the first tubular portion of the blood pump, and having a flange-shaped connector portion arranged at the distal end for fastening the connector to an organ;
  wherein the blood pump comprises a first, toothed portion and the connector comprises a second toothed portion corresponding to the first portion, such that the blood pump is rotationally fixed relative to the connector when the first and the second portion engage in one another.
17. A casing having a first lateral surface and at least one tongue protruding inwardly from the lateral surface for use in a blood pump for conveying blood, wherein the blood pump comprises a first tubular portion and a second tubular portion, and between the first and the second tubular portion there is provided a flange-shaped portion;
  wherein a locking ring that can be expanded in a guiding gap is arranged in the flange-shaped portion and is guided and configured in the guiding gap and engages by means of at least one tongue in a portion of the guiding gap or an opening leading to the guiding gap.
18. The system according to any one of the preceding aspects, wherein the first tubular portion is an inlet port of a blood pump.

The invention claimed is:
1. A system for connecting a blood pump to a heart, the system comprising:
  the blood pump for conveying blood, wherein the blood pump further comprises a flange-shaped portion, a first tubular portion, and a second tubular portion, wherein the flange-shaped portion is between the first and the second tubular portions;
  a connector including a tubular connector portion, a distal end, a proximal end, a lumen, and a flange-shaped connector portion, the tubular connector portion extending in an axial direction between the distal end and the proximal end, the lumen for receiving the first tubular portion of the blood pump, and the flange-shaped connector portion arranged at the distal end for fastening the connector to an organ; and
  a locking ring;
  wherein the blood pump further comprises a first toothed portion and the connector further comprises a second toothed portion corresponding to the first toothed portion, such that the blood pump is rotationally fixed relative to the connector when the first and the second toothed portions engage in one another; and
  wherein the locking ring is configured to axially hold the blood pump on the connector.
2. The system of claim 1, wherein the locking ring engages a side of a region arranged on the blood pump or on the connector.
3. The system of claim 1, wherein a wall of the tubular connector portion surrounding the lumen comprises an expansion having the form of a latching lug surrounding the wall, at least sectionally, wherein the locking ring is arranged in the flange-shaped portion of the blood pump and is expandable in a guiding gap, and is guidable in the guiding gap such that in a first state, the locking ring engages the wall on a first side of the expansion and, in a second, expanded state, does not engage the wall on the first side of the expansion, wherein the locking ring is configured to move axially from a second side of the expansion to the first side of the expansion in the expanded state.
4. The system of claim 3, wherein the expansion surrounds the wall fully.
5. The system of claim 3, wherein the latching lug comprises a flat portion at a proximal end, which flat portion corresponds with the flange-shaped portion of the blood pump.
6. The system of claim 3, wherein the guiding gap has a width corresponding to a height of the locking ring, such that the blood pump is fixed in the axial direction in the first state.
7. The system of claim 3, wherein the guiding gap is open in a radial direction.
8. The system of claim 3, wherein a portion of the flange-shaped portion of the blood pump further comprises a stop ring, which centres the locking ring in the second, expanded state.
9. The system of claim 3, wherein the locking ring comprises a portion engaging the first side of the expansion and a further portion angled relative to the portion engaging the first side of the expansion, wherein the angled portion of the locking ring is formed in such a way that the angled portion in the first state is radially supported on a partial segment of the flange-shaped portion or of the first tubular portion.
10. The system of claim 1, wherein the locking ring is fixed to one end of the blood pump.
11. The system of claim 1, wherein the locking ring is an open circlip.
12. The system of claim 1, wherein the flange-shaped portion of the blood pump comprises openings to the second tubular portion.
13. The system of claim 12, further comprising a casing that is configured to be drawn over the blood pump, the casing comprising at least one tongue, which protrudes into at least one of the openings.
14. The system of claim 1 further comprising a sealing element, wherein the first tubular portion further comprises a groove, in which the sealing element is arranged in such a way that the sealing element lies sealingly against an inner face of a wall of the tubular connector portion.
15. The system of claim 1, wherein the first tubular portion is an inlet port of the blood pump.

* * * * *